(12) United States Patent
Sohn et al.

(10) Patent No.: US 7,584,629 B2
(45) Date of Patent: Sep. 8, 2009

(54) SEPARATION OF A SUBSTANCE MIXTURE CONSISTING OF HYDROGEN CHLORIDE AND PHOSGENE

(75) Inventors: Martin Sohn, Mannheim (DE); Eckhard Stroefer, Mannheim (DE); Filip Nevejans, St. Gillis-Waas (BE); Ulrich Penzel, Tettau (DE); Hans-Juergen Pallasch, Kallstadt (DE); Peter Van Den Abeel, Brasschaat (BE); Filip Deberdt, Muizen (BE); Jan D. Jacobs, Baton Rouge, LA (US); Wolfgang Mackenroth, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 455 days.

(21) Appl. No.: 10/538,759

(22) PCT Filed: Dec. 13, 2003

(86) PCT No.: PCT/EP03/14188

§ 371 (c)(1),
(2), (4) Date: Jun. 10, 2005

(87) PCT Pub. No.: WO2004/056758

PCT Pub. Date: Jul. 8, 2004

(65) Prior Publication Data

US 2006/0123842 A1    Jun. 15, 2006

(30) Foreign Application Priority Data

Dec. 19, 2002    (DE) ................. 102 60 084

(51) Int. Cl.
*F25J 3/00*    (2006.01)
*C07C 69/96*   (2006.01)

(52) U.S. Cl. .............. 62/617; 560/347; 558/270; 558/274

(58) Field of Classification Search .............. 62/617; 560/347; 558/270, 274
See application file for complete search history.

(56) References Cited

U.S. PATENT DOCUMENTS 2,764,607 A    9/1956   Hieserman
3,142,535 A *  7/1964   Christoph, Jr. ........... 423/488
3,211,776 A   10/1965   Stephens
3,226,410 A   12/1965   Hettich et al.
3,381,025 A    4/1968   Mitsumori et al.
3,544,611 A * 12/1970   Michelet et al. ........... 560/347
3,574,695 A *  4/1971   Grant ..................... 560/347
4,278,788 A *  7/1981   Hatfield et al. ............ 528/494
6,348,613 B2 * 2/2002   Miyamoto et al. .......... 558/274
6,479,690 B1  11/2002   Garel et al.
2001/0041806 A1* 11/2001 Miyamoto et al. .......... 558/270

FOREIGN PATENT DOCUMENTS

| DE | 1 233 854 | 2/1967 |
| DE | 30 00 524 | 7/1981 |
| DE | 32 12 510 | 11/1982 |
| DE | 33 23 882 | 4/1984 |
| EP | 0 570 799 | 11/1993 |
| GB | 827376   | 2/1960 |
| JP | 09208589 | 8/1997 |
| SU | 1 811 161 | 5/1995 |
| WO | 95/30663 | 11/1995 |
| WO | 98/31662 | 7/1998 |

OTHER PUBLICATIONS

Kunststoff Handbuch, vol. 7 (Polyurethane), 3rd Edition, pp. 76-88, 1993.
I. I. Konstantinov and A. I. Kormucheshkina: "Kinetics of the Reactions of 2,4-Tolylene- and 4,4'-Diphenylmethanediamine Dihydrochloride Crystals with Phosgene Dissolved in Chlorobenzene" Xhurnal Prikladnoi Khimii, vol. 49, No. 3, pp. 596-599, 1976.

* cited by examiner

*Primary Examiner*—William C Doerrler
(74) *Attorney, Agent, or Firm*—Oblon, Spivak, McClelland, Maier & Neustadt, P.C.

(57) ABSTRACT

The invention relates to a process for the partial or complete separation of a mixture comprising hydrogen chloride and phosgene, possibly solvents and possibly low boilers and inerts as are typically obtained in the preparation of isocyanates by reaction of amines with phosgene, which comprises firstly carrying out a partial or complete condensation of phosgene, then a distillation or stripping step in a column to remove the hydrogen chloride from the bottom product phosgene and subsequently a scrub of the top product hydrogen chloride by means of the process solvent to absorb the phosgene in the process solvent. An after-purification by means of adsorption on activated carbon or by another suitable method can subsequently be carried out to remove solvent residues.

16 Claims, No Drawings

SEPARATION OF A SUBSTANCE MIXTURE CONSISTING OF HYDROGEN CHLORIDE AND PHOSGENE

The invention relates to a process for the partial or complete separation of a gaseous or completely or partly condensed mixture of hydrogen chloride (HCl), phosgene (COCl$_2$) and possibly inert gases and/or low boilers such as nitrogen, by-products from the phosgene synthesis, e.g. carbon monoxide, chlorine, methane, carbon tetrachloride (CCl$_4$) and chloroform (CHCl$_3$) and other low-boiling components and also solvent which is intentionally or unintentionally present, e.g. chlorinated, preferably aromatic hydrocarbons such as dichlorobenzene, chlorobenzene, trichlorobenzene, aromatic or aliphatic hydrocarbons such as toluene, xylene, benzene, pentane, hexane, heptane, octane, cyclohexane, biphenyl, ketones such as 2-butanone, methyl isobutyl ketone, esters such as diethyl isophthalate, ethyl acetate, butyl acetate, nitriles such as acetonitrile or sulfolane, as is typically obtained in the reaction of aliphatic or aromatic amines with phosgene to form the corresponding isocyanates.

Similar mixtures of phosgene and hydrogen chloride are also obtained, for example, in the preparation of chlorinated organic compounds such as acid chlorides or chloroformates.

Aromatic isocyanates such as TDI (tolylene diisocyanate) and MDI (methylenedi(phenyl isocyanate)) or PMDI (polymethylene-polyphenylene polyisocyanate) and aliphatic isocyanates, such as HDI (hexamethylenedi(phenyl isocyanate)) and IPDI (isophorone diisocyanate) are prepared industrially around the world by reaction of the corresponding amines with phosgene. In these syntheses, hydrogen chloride is liberated as by-product in the process, usually in gaseous form. In addition, a more or less large excess of phosgene is generally used in the reaction, so that the phosgene used does not react completely with the amine despite high chemical yields in the production of isocyanates. At least part of the excess phosgene generally turns up in gaseous form together with the hydrogen chloride liberated and part or all of it is separated off from the reaction mixture together with the hydrogen chloride. Depending on the method of separation, more or less large amounts of solvent can also be separated off or entrained with the mixture of hydrogen chloride and phosgene. It is also possible for inert gases and low boilers such as nitrogen which may have been carried over from the phosgene synthesis or have been deliberately added or introduced as a result of the nature of the process to be present in the mixture of hydrogen chloride and phosgene. These can, however, also be separated off from the mixture of hydrogen chloride and phosgene beforehand or afterwards. To operate an isocyanate synthesis economically, it is absolutely necessary to separate the mixture of hydrogen chloride and phosgene, recirculate the excess phosgene to the isocyanate synthesis or to another use and pass the hydrogen chloride which has been separated off to a further use or dispose of it. This further use of the hydrogen chloride can be, for example, an oxychlorination for preparing vinyl chloride, a Deacon process for the recovery of chlorine which can be reused for the synthesis of phosgene or the production of aqueous hydrochloric acid. The hydrogen chloride obtained in the isocyanate synthesis has to meet specific purity requirements, especially in the case of use for oxychlorination or for the Deacon process, so that the separation of phosgene and hydrogen chloride has to be carried out using process variants in which it is ensured that the hydrogen chloride after separation and work-up contains only small amounts of by-products, in particular chlorinated solvents such as dichlorobenzene or chlorobenzene. These chlorinated aromatic compounds generally deactivate the catalyst in oxychlorinations. Furthermore, they, like phosgene, interfere in the production of aqueous hydrochloric acid for the food industry or other applications. In addition, residual amounts of phosgene in the hydrogen chloride pose a not inconsiderable hazard potential and health risk.

The continuous preparation of organic isocyanates by reaction of primary organic amines with phosgene has been described many times and is carried out on an industrial scale. It is described, for example, in the Kunststoffhandbuch, Volume 7 (Polyurethane), 3rd revised edition, Carl Hanser Verlag, Munich-Vienna, p. 76 ff (1993). In the customary embodiment of the process, the mixture of phosgene and hydrogen chloride formed is usually separated by partial or complete condensation of the phosgene, by distillation or by absorption of phosgene in an inert solvent.

In general, phosgene is firstly partly condensed out from the mixture of phosgene and hydrogen chloride. The separation is therefore usually carried out either under a high pressure, preferably 10-50 bar, or at very low temperatures, preferably about −30° C. At high pressures, phosgene can be condensed out easily and inexpensively, for example by use of cooling water. This is economically advantageous, but the high pressure poses a great safety risk in the case of a leakage, as has been described in DE 3212510. Low temperatures for separating phosgene and hydrogen chloride are generally associated with low pressures, but considerable energy has to be expended to produce the low temperatures. Furthermore, in accordance with Henry's law, the solubility of hydrogen chloride in phosgene is very high, so that recirculated phosgene contains relatively large amounts of hydrogen chloride. This can lead to formation of amine hydrochloride in the phosgenation of the amine. The phosgenation of amine hydrochlorides requires longer residence times and higher excesses of phosgene and consequently implies a higher phosgene holdup.

One possible way of separating the mixtures described is distillation. U.S. Pat. No. 3,544,611 describes a process for preparing organic isocyanates at a pressure in the range from 10 to 50 bar. It was surprisingly found that carrying out the reaction at relatively high pressures, at least 10 atm gauge, leads to increased yields of isocyanate. Furthermore, higher pressures aid the separation of phosgene and hydrogen chloride. The first reaction step for the preparation of isocyanates, viz. the reaction between amine and phosgene to form the intermediate carbamoyl chloride, is carried out in a mixing circuit. The second reaction step, viz. the decomposition of the carbamoyl chloride to give the isocyanate, is carried out in a reaction column installed downstream of the mixing circuit, giving a mixture of phosgene and hydrogen chloride at the top of the column. Phosgene is condensed from this mixture in two stages, with the first condenser for partial condensation being operated by means of cooling water and the second condenser for virtually complete condensation being operated using brine at a very low temperature. The condensed phosgene is returned to the top of the column. The phosgene is then taken off again at a liquid offtake in the enrichment section of the column and is returned to the reaction in the mixing circuit.

The separation of the residual phosgene from the reaction mixture which is taken off at the bottom of the reaction column is carried out in a further column. In the latter, phosgene is taken off at the top, condensed in two stages using cooling water and brine in a manner analogous to the first column and returned to the mixing circuit for the reaction. Since the reaction is completed in the reaction column, this phosgene taken off at the top of the second column contains only the hydrogen chloride which was dissolved in the reaction mixture at the inlet to the residual phosgene separation column.

A disadvantage of this process is that only part of the phosgene can be condensed out of the hydrogen chloride to minimize the phosgene loss. Complete separation by condensation without rectification is not possible, so that relatively large amounts of phosgene are lost and, furthermore, the hydrogen chloride produced is strongly contaminated with phosgene. Both the phosgene taken off at the side offtake of the reaction column and that taken off at the top of the residual phosgene separation column contain hydrogen chloride. The concentration is in each case determined according to Henry's law from the pressure, temperature and composition of the gaseous and liquid phases. A further disadvantage is the high pressures which pose a high hazard potential in the case of a leakage.

U.S. Pat. No. 3,544,611 describes an alternative separation of phosgene and hydrogen chloride at pressures of from 15 bar to 50 bar or higher with condensation and discharge of liquid hydrogen chloride. The vapor from the isocyanate synthesis reactor is fed into a small side column at whose upper end liquid hydrogen chloride is taken off. In a manner analogous to the above-described process variant, the reaction to form the isocyanate is carried out in a mixing circuit and a downstream reaction column. Likewise in an analogous manner, the major part of the phosgene is condensed in a dephlegmator at the top of the reaction column and is returned to the column. The mixture of phosgene and hydrogen chloride taken off from the dephlegmator is fed into the above-described side column which is operated at the same pressure as the reaction column. Hydrogen chloride is condensed in the condenser at the top of this side column and part of it is returned to this column as runback and the other part is taken off in liquid form for further use. The column has a pure enrichment section but no stripping section and bottom circulation vaporizer and thus serves only to purify the hydrogen chloride. The purification of the phosgene taken off at the bottom of this column is carried out by recirculation to the top of the reaction column. Liquid phosgene is taken off at a liquid offtake on the reaction column in a manner analogous to the above-described first process variant and is passed to the amine-phosgene reaction in the mixing circuit. Likewise in a manner analogous to the first process variant described, the residual phosgene is taken off at the top of a residual phosgene separation column following the reaction column, condensed in two stages and recirculated to the mixing circuit for reaction in the amine-phosgene reaction.

A disadvantage of this process is that the second column for separating off and purifying the hydrogen chloride in the side column is operated at the same pressure level as the reaction column in which the reaction to give the isocyanate takes place. This results in undesirable coupling of reaction section and work-up section. It can be more advantageous to carry out the separation of phosgene and hydrogen chloride at higher or lower pressures than the reaction. Thus, high pressures in U.S. Pat. No. 3,544,611, which are advantageous for the separation of phosgene and hydrogen chloride, also mean high temperatures in the reaction section of the isocyanate synthesis, which lead to secondary reactions and considerably reduce the yield of isocyanate. Furthermore, the reaction column is used for purifying the phosgene by removing residual hydrogen chloride in the enrichment section of the reaction column. This is likewise an undesirable coupling. Furthermore, the phosgene which is taken off at the liquid offtake of the reaction column and is intended for the amine-phosgene reaction becomes saturated with hydrogen chloride. In accordance with the gas/liquid equilibrium, the hydrogen chloride concentration corresponding to the pressure and temperature at this point is established in the liquid phase, viz. the phosgene. Since the pressure and the temperature in the reaction column are determined by the reaction, it is not possible to set more favorable conditions under which, for example, the concentration of the hydrogen chloride in the phosgene is significantly lower independently of the reaction.

A particular disadvantage of the second process variant is the condensation of the hydrogen chloride which, despite the high pressures, is carried out at very low temperatures with a high energy consumption. In the case of leakage, the high pressures pose a high hazard potential. The fact that hydrogen chloride is obtained as liquid is also energetically disadvantageous. In general, the hydrogen chloride obtained in isocyanate production is processed further in gaseous form, for example in an oxychlorination to produce ethylene dichloride, so that the hydrogen chloride has to be vaporized again with further consumption of energy.

GB 827376 describes a continuous process for preparing aromatic isocyanates by reaction of an amine in free form or as salt which can readily be decomposed to the free amine with a solution of phosgene at a pressure of greater than $3*10^5$ Pa, in which the reactants are introduced simultaneously with mixing into the lower end of a vertical tube reactor in which the reaction products rise rapidly to the upper end. The liquid phase is collected in a container from which it is taken off for isolation of the isocyanate. This container can be a phase separation apparatus which is operated under the same pressure, is connected via an overflow tube to the liquid outlet and has a throttle valve in the liquid outlet. The liquid separated off in the container is fed to a column which is operated under atmospheric or superatmospheric pressure and elevated temperature and in which residual phosgene and hydrogen chloride are separated off at the top in gaseous form. The excess phosgene is condensed from the mixture of phosgene and hydrogen chloride separated off in the container, and the hydrogen chloride which has been separated off in this way is depressurized and discharged. The reactants are fed into the tube reactor by means of a joint pump or two separate pumps or are mixed in a Venturi mixing nozzle and from there introduced into the tube reactor. The temperature in the tube reactor is said to be 80-200° C. and the pressure is greater than $3*10^5$ Pa, at most the vapor pressure of the reaction mixture and preferably from 15 to $20*10^5$ Pa.

A disadvantage is the very low purity of the hydrogen chloride, since considerable amounts of phosgene remain in the hydrogen chloride in a single-stage condensation at the preferred pressures of from 15 to $20*10^5$ Pa and these are very troublesome in further use of the hydrogen chloride for oxychlorination, for a Deacon process or for producing aqueous hydrochloric acid. A further disadvantage is the high hydrogen chloride content of the phosgene condensed out, which is recycled to the reaction without further purification.

U.S. Pat. No. 3,381,025 describes a process for preparing methylenebis(phenyl 4-isocyanate) (MDI), tolylene 2,4-diisocyanate (TDI), polymethylene-poly(phenyl isocyanate) (polymeric MDI). Use is made here of the principle of evaporative cooling, i.e. a mixture of solvent, phosgene and hydrogen chloride vaporizers at the reaction temperature. An advantage of this is that the partial pressure of the phosgene is reduced by the presence of the solvent and phosgene can therefore be condensed more easily. The condensation of the phosgene together with the chlorobenzene used as solvent is achieved by cooling the gas mixture. The phosgene/solvent mixture is recirculated to the reaction, and the hydrogen chloride together with residual amounts of phosgene is removed in an absorber. A 22% strength by weight mixture of phosgene in chlorobenzene is obtained. A disadvantage of this process is the condensation of the phosgene/solvent mixture by cooling to the very low temperature of −30° C. Furthermore, the high loss of phosgene in the discharged hydrogen chloride of 3.4 mol % of phosgene in the hydrogen chloride is economically disadvantageous and poses safety problems. For most applications such as oxychlorination, a Deacon process or the preparation of hydrochloric acid, it is not possible to use this hydrogen chloride stream. A further disadvantage is the high hydrogen chloride content of the phosgene/solvent mixture obtained, since the solubility of hydrogen chloride in this mixture at low temperatures is particularly high.

In U.S. Pat. No. 3,381,025, the phosgenation of an organic primary amine to form the corresponding isocyanate is carried out in two stages at a temperature of <60° C. in the first stage and from 100 to 190° C. in the second stage. A mixture of the inert solvent, excess phosgene and the hydrogen chloride formed is taken off from the second stage and the hydrogen chloride is separated off from this by cooling the mixture to −20° C. The cold mixture of phosgene and solvent obtained is recirculated to the first reaction stage. A disadvantage here is the intensive cooling of the mixture which is necessary, so that high energy costs and capital costs for refrigeration equipment are incurred. This cooling is particularly disadvantageous when the mixture has to be reheated to the reaction temperature. A further disadvantage is the high hydrogen chloride content of the phosgene/solvent mixture obtained.

WO 99/11597 describes the separation of hydrogen chloride and phosgene under superatmospheric pressure in a column which is installed downstream of a reactor for the preparation of chloroformate. The reactor is operated at pressures of from 2 to 60 bar, preferably from 6 to 40 bar. High pressures are recognized as advantageous for the separation of phosgene and hydrogen chloride, since the condensers then do not have to be operated at low temperatures.

A further possible way of separating phosgene and hydrogen chloride is scrubbing. SU 1811161 describes a process for preparing isocyanates by reaction of amines with phosgene. For the reaction with the amine, a solution of phosgene in chlorobenzene as solvent is prepared by absorption of gaseous phosgene in chlorobenzene. The advantage is the saving in energy costs, since only a one-off condensation and no further vaporization of the phosgene is required. Amine and phosgene solution are reacted in a reactor. In a phase separator, gas phase and liquid phase comprising isocyanate, chlorobenzene and phosgene are separated. The gas phase taken from the phase separator comprises hydrogen chloride, phosgene and chlorobenzene and is partially condensed and passed to an absorber. The liquid phase is fed to a stripping column in which hydrogen chloride and phosgene are separated off at the top, partially condensed and then likewise passed to the absorber. The incondensible gas from the stripping column is passed to the phosgene synthesis. In the absorber, the phosgene is absorbed in chlorobenzene which has been distilled off from the isocyanate/chlorobenzene mixture. The phosgene/chlorobenzene stream contains about 70% by weight of phosgene and is combined with a phosgene/chlorobenzene stream from the synthesis of phosgene with subsequent absorption in chlorobenzene and the combined stream is used as phosgene solution for the amine-phosgene reaction. The hydrogen chloride stream going over at the top of the absorber is passed to further treatment, since it still contains about 4% by weight of phosgene.

The document says nothing about temperatures and pressures at which the absorber or the reactor are operated. A disadvantage of the process described in SU 1811161 is the low purity both of the gaseous hydrogen chloride obtained, which contains about 4% by weight of phosgene, and also the liquid phosgene/chlorobenzene solution which contains relatively large amounts of hydrogen chloride because of the low temperatures of the chlorobenzene used for scrubbing. Owing to the high phosgene concentration, the hydrogen chloride stream cannot be used for the customary purposes, e.g. oxychlorination, the Deacon process or the production of hydrochloric acid. It is generally known and also published, inter alia, in I. I. Konstantinov, A. I. Kormucheshkina, Zhurnal Prikladnoi Khimii, 49 (3), pp. 596-599, 1976, and DE 3212510, U.S. Pat. No. 3,574,695 or DE 3323882 that hydrogen chloride reacts with amines in the phosgenation to form hydrochlorides whose conversion into the isocyanate requires considerably longer residence times, high phosgene excesses and high temperatures. In addition, increased by-product formation is observed. The saturation of the phosgene solution with hydrogen chloride for the reaction leads to larger apparatuses, a higher phosgene holdup, a higher energy consumption and a reduced yield.

EP 0570799 describes a process in which the reaction between amine and phosgene to give the isocyanate is carried out in the gas phase. The hydrogen chloride/phosgene mixture formed is separated by means of condensation, absorption of phosgene in an inert solvent, for example chlorobenzene or dichlorobenzene, maintained at from −10° C. to 8° C., or by adsorption and hydrolysis on activated carbon.

U.S. Pat. No. 3,226,410 describes a continuous process for preparing aromatic isocyanates by mixing a stream of an aromatic amine into a phosgene stream in a tube reactor at Reynolds numbers of greater than 2100, preferably 5000-2 000 000, and temperatures of from 60 to 90° C., preferably from 80 to 85° C. The amount of phosgene is at least 1 mol, preferably from 6 to 12 mol, per mole of amine. The reaction solution is then, if desired after pretreating, transferred to a second reactor which is configured as a vessel or column and is at from 110 to 135° C., preferably from 110 to 120° C. The amine concentration is from 2 to 25% by weight, preferably from 5 to 10% by weight, and the phosgene concentration is from 10 to 100% by weight, preferably from 10 to 60% by weight. The pressure under which the phosgene stream is fed into the tube reactor is from 50 to 170 psig. The liquid phase comprising isocyanate, solvent, relatively small amounts of by-products, hydrogen chloride and phosgene dissolved in the solvent is taken off from the second reactor separately from the gas phase comprising hydrogen chloride, solvent, phosgene and traces of isocyanate. Solvents used are chlorinated hydrocarbons which are inert and have a boiling point lower than that of the isocyanate. Particular preference is given to chlorobenzene. The second reactor, which is operated at a pressure of 45 psig or above, is followed by a residence vessel and a buffer vessel from which the liquid phase is conveyed under level control to a column for removal of excess phosgene. Phosgene, hydrogen chloride and solvent are taken off at the top and recirculated to the phosgene container. The bottom product, comprising isocyanate and solvent, is fed to a single-stage removal of solvent by distillation. The solvent which has been separated off from the isocyanate is used for absorption of the residual phosgene from the hydrogen chloride stream. The phosgene taken off in the second reactor and in the buffer vessel is condensed in two stages and recirculated to the phosgene container. The uncondensed phosgene/hydrogen chloride mixture is fed to a scrubber which is supplied with solvent recovered in the solvent removal. The gas which has not been absorbed, mainly hydrogen chloride, is subsequently reacted with water in an absorber to give aqueous hydrochloric acid.

Chemical separation of phosgene and hydrogen chloride is also known. WO 9831662 describes the preparation of 3-(isocyanatomethyl)hexamethylene 1,6-diisocyanate by phosgenation of the corresponding amine. A tertiary amine is added as hydrogen chloride scavenger and precipitates as amine hydrochloride. The slurry is distilled in the presence of a hydrogen chloride scavenger. In DE 1233854, too, the hydrogen chloride formed is bound by addition of a tertiary amine. The addition of organic nitrogen bases is also employed in DE 3000524 and U.S. Pat. No. 3,211,776.

In JP 09208589, an alkali metal compound or alkaline earth metal compound, preferably a weakly acidic salt or oxide such as calcium oxide, is used for scavenging the hydrogen chloride formed in the reaction.

WO 9530663 describes the synthesis of functionalized 1,3,5-triazine isocyanates in which at least part of the hydrogen chloride is likewise bound chemically during the reaction.

A disadvantage of these processes is the solids formed, which are difficult to handle from a chemical engineering point of view. The work-up is made considerably more difficult since the ammonium salts formed frequently crystallize out. Furthermore, the introduction of an additional auxiliary makes the process uneconomical. The auxiliaries can also result in formation of various by-products in the phosgenation, which reduce the quality of the desired isocyanate.

It is an object of the present invention to separate mixtures of phosgene and hydrogen chloride inexpensively, i.e. with a low energy consumption, and with a low hazard potential from a safety point of view into hydrogen chloride having a good purity and pure phosgene.

If dissolved hydrogen chloride remains in the recirculated phosgene in the separation of phosgene and hydrogen chloride, this reacts directly with the free amine in the first stage of the phosgenation to form amine hydrochloride. However, the reaction rate of the hydrochloride phosgenation is considerably lower than that of the free amine, as described in I. I. Konstantinov, A. I. Kormucheshkina, Zhurnal Prikladnoi Khimii, 49 (3), pp. 596-599, 1976. In addition, the reaction of amine hydrochlorides with phosgene to form the isocyanate requires higher temperatures and therefore tends, as described in GB 1212249, to give increased by-product formation, in particular the formation of ureas. Avoiding the formation of amine hydrochlorides thus leads to smaller apparatuses, a lower phosgene holdup, a lower energy consumption and higher yields. Since the solubility of amine hydrochlorides in the respective reaction mixtures and also in most commercially available solvents is very low, formation of hydrochloride also leads to the problem of solids formation. It is therefore important that the solutions of amine and phosgene which are reacted contain no dissolved hydrogen chloride.

The hydrogen chloride formed in situ by the reaction of amine with phosgene can likewise form amine hydrochloride in a subsequent reaction with the amine still present. However, it has been found that there is a considerable difference in the order of magnitude of hydrochloride formation and also the further reaction with phosgene depending on whether the hydrogen chloride is brought into contact with the amine which is present in high concentration immediately at the beginning of the reaction and forms amine hydrochloride, which precipitates as a solid, virtually quantitatively, or whether hydrogen chloride formed only in the course of the reaction reacts with the amine which is then only present in a very low concentration to form amine hydrochloride. The reaction between amine and phosgene is extremely fast even at low temperatures, so that the amine concentration drops sharply at the beginning of the reaction. Amine hydrochloride from hydrogen chloride formed in situ displays high supersaturation in the reaction mixture, with the isocyanate which is already present in a relatively high concentration acting as solubilizer. It therefore reacts relatively quickly with phosgene to form carbamoyl chloride, in contrast to amine hydrochloride which has been formed directly from amine and hydrogen chloride and has precipitated as a solid.

The present invention accordingly provides a process for the partial or complete separation of a mixture comprising hydrogen chloride and phosgene, possibly solvents, low boilers and inerts as are typically obtained in the preparation of isocyanates by reaction of amines with phosgene, which comprises firstly carrying out a partial or complete condensation of phosgene, then a distillation or stripping step in a column to remove the hydrogen chloride from the bottom product phosgene and subsequently a scrub of the top product hydrogen chloride by means of the process solvent to absorb the phosgene in the process solvent. To remove solvent residues from the phosgene and/or hydrogen chloride, they can subsequently be purified further by means of adsorption, for example on activated carbon, or by other suitable methods.

In the process of the present invention, the partial or complete separation of a mixture of hydrogen chloride and phosgene and possibly the other components mentioned is carried out by partial condensation, in one or more stages and at various temperature and pressure levels, subsequent distillation or stripping in a column to remove hydrogen chloride from the phosgene and subsequent absorption of the phosgene remaining in the hydrogen chloride stream in the process solvent. The latter is preferably chlorobenzene, dichlorobenzene, mixtures of the two or toluene.

Largely pure hydrogen chloride is obtained at the top of the absorber, and this can be passed to a further use. The phosgene stream obtained at the bottom of the distillation column is recirculated to the isocyanate synthesis, preferably for reaction with the amine in the first stage, for example in a static mixer. However, it can also be fed to another apparatus of the reaction section or work-up section. The phosgene/scrubbing medium stream obtained at the bottom of the absorber is likewise recirculated to the isocyanate synthesis, i.e. to the first reactor or one of the subsequent reactors or to a column for phosgene separation or for work-up of the reaction mixture. In particular, this stream can be used as runback for a column, for example a reaction column. This is particularly advantageous because it comprises not only phosgene and the scrubbing medium but also hydrogen chloride which would lead to amine hydrochloride if recirculated to the first reactor. If desired, the hydrogen chloride stream leaving the absorber can be subjected to an after-purification, in particular an adsorption on activated carbon, a pressure swing adsorption, a further scrubbing step or some other after-purification process. Undesirable components, in particular chlorinated hydrocarbons such as the solvents dichlorobenzene or chlorobenzene can be removed from the hydrogen chloride stream in this way.

The mixture of phosgene and hydrogen chloride used for the process of the present invention usually comprises hydrogen chloride and phosgene together with, possibly, solvents such as dichlorobenzene, chlorobenzene, toluene or others and, possibly, low boilers and inerts such as nitrogen, carbon monoxide, methane, carbon tetrachloride or chloroform.

The partial condensation of phosgene from the resulting mixture comprising hydrogen chloride, phosgene, possibly solvents and inerts is carried out in one stage or preferably more than one stage at −40° C., achievable by means of refrigerants, to 40° C., achievable by means of cooling water, depending on the pressure in the reaction section. The distillation to remove hydrogen chloride from the recirculated phosgene is carried out at a temperature at the bottom of from 5 to 150° C., preferably from 5 to 50° C., a pressure at the top of from 1 to 35 bar, preferably from 1.5 to 4.0 bar and a temperature at the top of from −20° C. to 30° C., preferably from −10° C. to 0° C. As an alternative, the hydrogen chloride can also be removed from the recirculated phosgene by stripping with an inert gas such as nitrogen, the process solvent vapor, phosgene or another gaseous or vaporizable substance. The temperature at the top of the absorber is from −40° C. to 10° C., preferably from −15° C. to 0° C., the temperature at the bottom is from −10° C. to 30° C., preferably from 0 to 10° C., and the pressure at the top is from 1 to 35 bar, preferably from 1.5 to 4.0 bar. The absorption medium stream can advantageously be saturated with hydrogen chloride beforehand, so that saturation of the absorption medium with hydrogen chloride does not take place in the scrubber. The liberated heat of solution of hydrogen chloride in the absorption medium stream can then be removed externally in a heat exchanger. Removal of the liberated heat of the solution of hydrogen chloride in the absorption medium stream can alternatively be carried out using intermediate cooling on the absorber.

The upstream partial condensation is advantageous from an energy point of view, since the condensation can be carried out stepwise at various temperature and, if appropriate, pressure levels. The subsequent distillation gives a phosgene stream which is largely free of hydrogen chloride at the bottom, so that considerably less amine hydrochloride can be formed in the reaction with amine.

The advantage of the subsequent absorption of phosgene from the hydrogen chloride stream is a saving in energy costs, since condensation and renewed vaporization of the phosgene remaining in the hydrogen chloride stream is not necessary. Particular energy savings can be achieved by feeding the phosgene-containing output from the absorber to the phosgenation reactor as feed or, if appropriate, to a reaction column or a column for phosgene separation or for work-up of the reaction mixture as runback. In the latter cases, it may in this way be possible to omit the condenser at the top of the column and dispense with the partial or complete condensation of the vapor stream for generating runback. This considerably reduces the energy consumption.

The invention is illustrated by the following example.

EXAMPLE

The separation of a hydrogen chloride/phosgene mixture was carried out by partial condensation, distillation in a bubble cap tray column and subsequent absorption in a downstream scrubber, by means of which very pure phosgene can be produced at the bottom outlet of the distillation column and pure hydrogen chloride can be produced at the top outlet of the scrubber in an economically advantageous manner and at the same time at low pressures and thus a reduced hazard potential. Solvent residues are removed by means of adsorption from the hydrogen chloride which has been separated off in this way.

1) Partial Condensation of Phosgene:

The partial condensation of phosgene from a stream from an isocyanate synthesis was carried out in two successive heat exchangers at 33° C. (cooling water) and at −15° C. (brine). The hydrogen chloride/phosgene mixture used had a flow rate of 3.26 kg/h. The stream used comprised phosgene, hydrogen chloride, chlorobenzene and the low boilers and inerts typical for an isocyanate synthesis. The composition was 2.43 kg/h of phosgene (74.6% by weight), 0.235 kg/h of hydrogen chloride (7.2% by weight), 0.56 kg/h of chlorobenzene (17.3% by weight), 0.0106 kg/h of $CCl_4$ (0.3% by weight), 0.0169 kg/h $CHCl_3$ (0.5% by weight), 0.001 kg/h of carbon dioxide (0.02% by weight) and small amounts of nitrogen (4 ppm). The mixture obtained was fed as a two-phase mixture into the middle part of the downstream distillation column.

2) Distillation to Remove Hydrogen Chloride from the Phosgene so as to Recover Very Pure Phosgene:

A bubble cap tray column having 33 bubble cap trays, 22 in the stripping section and 11 in the enrichment section, was used. The diameter of the column was 55 mm. The pressure at the top was 2.5 bar abs. and the temperature at the bottom was 38° C. The temperature at the top of the column was −9° C. A Robert vaporizer was used as vaporizer and a shell-and-tube apparatus having 13 tubes was used as condenser at the top.

The mixture obtained from the partial condensation was fed into the column between the stripping and enrichment sections. The feed temperature was 24.5° C. The feed, viz. the hydrogen chloride/phosgene/chlorobenzene mixture, was introduced between the stripping and enrichment sections.

At the bottom, a total stream of 5.53 kg/h comprising 4.9 kg/h of phosgene (89% by weight), 0.0005 kg/h of hydrogen chloride (100 ppm), 0.57 kg/h of chlorobenzene (10% by weight), 0.02 kg/h of $CHCl_3$ (0.3% by weight) and 0.01 kg/h of $CCl_4$ (0.2% by weight) was taken off. The phosgene/chlorobenzene mixture taken off at the bottom of the column thus contained only small traces of hydrogen chloride, i.e. the phosgene was very pure in respect of hydrogen chloride. The inert solvent chlorobenzene does not interfere in the recirculation to the reaction section.

The phosgene/hydrogen chloride stream taken off at the top of the column was partially condensed in the condenser at the top and was returned to the column as runback. The amount of runback was 0.2 kg/h and its temperature was −20° C. The incondensible stream of 1.24 kg/h passing the condenser at the top had the following composition: 0.92 kg/h of hydrogen chloride (74% by weight), 0.32 kg/h of phosgene (26% by weight), 0.2% by weight of carbon dioxide, 0.001 kg/h of carbon monoxide (800 ppm) and small amounts of nitrogen (140 ppm).

3) Absorber (Scrubber):

Removal of Phosgene by Scrubbing the Hydrogen Chloride Stream

A packed column which had a diameter of 30 mm and had three sections of packing containing 3×3 mm wire mesh rings was used. The bed height was 630 mm per section. The pressure at the top was 2.2 bar abs. and the temperature at the bottom was 6° C. The temperature at the top of the column was −8° C. The column was equipped with a condenser at the top. A demister was installed in the top of the column to avoid entrainment of droplets.

The hydrogen chloride/phosgene feed stream had a flow of 1.24 kg/h and had the abovementioned composition. The feed temperature was −20° C. A chlorobenzene stream having a temperature of −25° C. and a flow of 1.32 kg/h was introduced at the top of the scrubber. The composition was 1.3 kg/h of chlorobenzene (99.6% by weight), 0.003 kg/h of $CCl_4$ (0.2% by weight) and 0.002 kg/h of $CHCl_3$ (0.2% by weight). Intermediate cooling was used to remove the liberated heat of solution of hydrogen chloride in the chlorobenzene scrubbing medium. The intermediate cooler was operated at −30° C.

The vapor stream obtained at the top of the scrubber was passed to the condenser at the top at which, in particular, entrained droplets were precipitated. The condensible fraction was recirculated to the bottom of the scrubber. The incondensible fraction of 0.87 kg/h had a composition of 0.86 kg/h of hydrogen chloride (99.5% by weight), 0.001 kg/h of phosgene (0.1% by weight), 0.001 kg/h of chlorobenzene (0.1% by weight), 0.001 kg/h of carbon dioxide (0.1% by weight), 0.001 kg/h of carbon monoxide (0.1% by weight) and 0.0005 kg/h of $N_2$ (500 ppm) and in each case small amounts of $CCl_4$ and $CHCl_3$ phosgene (each 80 ppm). The condenser at the top was operated at −30° C. The hydrogen chloride stream obtained in this way is very pure (99.9% by weight). The chlorobenzene/phosgene stream of 1.69 kg/h taken off at the bottom of the column has the composition 0.32 kg/h of phosgene (19% by weight), 1.3 kg/h of chlorobenzene (78% by weight), 0.05 kg/h of hydrogen chloride (3% by weight), 0.0027 kg/h of $CCl_4$ (0.2% by weight), 0.002 kg/h of $CHCl_3$ (0.1% by weight) and small amounts of nitrogen (60 ppm).

4) After-Purification of Hydrogen Chloride from the Hydrogen Chloride/Phosgene Separation The gaseous output from the top of the absorber was passed through an activated carbon filter in which residual phosgene and chlorobenzene were adsorbed on the activated carbon. A very pure hydrogen chloride stream in which no phosgene or chlorobenzene could be detected by in-line IR or GC analysis was obtained.

We claim:

1. A process for the partial or complete separation of a mixture comprising hydrogen chloride and phosgene, which comprises:
    firstly carrying out a partial or complete condensation of phosgene;
    then distillation or stripping in a column to remove the hydrogen chloride from the bottom product phosgene; and
    subsequently a scrub of the top product hydrogen chloride by a process solvent to absorb the phosgene in the process solvent.

2. The process as claimed in claim 1, wherein the partial or complete condensation of phosgene is carried out at from −40° C. to 40° C. and pressures of from 1 to 35 bar.

3. The process as claimed in claim 1, wherein the distillation to remove hydrogen chloride from phosgene is carried out at a temperature of the bottom of from 5 to 150° C., a pressure at the top of from 1 to 35 bar, and a temperature at the top of from −20° C. to 30° C.

4. The process as claimed in claim 1, wherein the hydrogen chloride is removed from the phosgene by stripping with an inert gas.

5. The process as claimed in claim 1, wherein the absorption or scrub is carried out by the process solvent.

6. The process as claimed in claim 1, wherein the temperature at the top of the absorber is from −40° C. to 10° C., the temperature at the bottom is from −10° C. to 30° C., and the pressure at the top is 1-35 bar.

7. The process as claimed in claim 1, wherein an absorption medium stream for the absorption has been saturated beforehand with hydrogen chloride.

8. The process as claimed in claim 1, wherein the heat of condensation of hydrogen chloride and phosgene in an absorption medium is removed by intermediate cooling in the absorber.

9. The process as claimed in claim 1, wherein an after-purification by adsorption is carried out.

10. The process as claimed in claim 1, wherein the scrub is carried out by chlorobenzene.

11. The process as claimed in claim 1, wherein the bottom product phosgene is recirculated to the reaction section of an isocyanate synthesis.

12. A runback in distillation or reaction columns, or a scrubbing solution for absorbers or scrubbers, comprising the bottom product phosgene as claimed in claim 1.

13. The process as claimed in claim 1, wherein the hydrogen chloride obtained is subsequently compressed.

14. The process as claimed in claim 1, wherein the hydrogen chloride obtained is subsequently added in a preparation of ethylene dichloride or a Deacon process.

15. The process as claimed in claim 1, wherein the mixture further comprises solvents, low boilers, and inert gases obtained in a preparation of isocyanates by reaction of amines with phosgene.

16. The process as claimed in claim 7, wherein a heat of condensation has been removed.

* * * * *

UNITED STATES PATENT AND TRADEMARK OFFICE
CERTIFICATE OF CORRECTION

PATENT NO. : 7,584,629 B2 Page 1 of 1
APPLICATION NO. : 10/538759
DATED : September 8, 2009
INVENTOR(S) : Sohn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 905 days.

Signed and Sealed this

Fourteenth Day of September, 2010

David J. Kappos
*Director of the United States Patent and Trademark Office*